(12) United States Patent
Kalyanraman et al.

(10) Patent No.: US 10,539,699 B2
(45) Date of Patent: Jan. 21, 2020

(54) CEMENT EVALUATION USING THE INTEGRATION OF MULTIPLE MODES OF ACOUSTIC MEASUREMENTS

(71) Applicant: Schlumberger Technology Coporation, Sugar Land, TX (US)

(72) Inventors: Ram Sunder Kalyanraman, Clamart (FR); Hiroshi Hori, Clamart (FR)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 159 days.

(21) Appl. No.: 15/333,675

(22) Filed: Oct. 25, 2016

(65) Prior Publication Data
US 2017/0139072 A1 May 18, 2017

(30) Foreign Application Priority Data
Nov. 16, 2015 (EP) ..................................... 15290288

(51) Int. Cl.
*G01V 1/40* (2006.01)
*G01V 3/18* (2006.01)
(Continued)

(52) U.S. Cl.
CPC ................ *G01V 1/50* (2013.01); *E21B 33/14* (2013.01); *E21B 47/0005* (2013.01);
(Continued)

(58) Field of Classification Search
CPC .. G01V 1/50; G01V 1/52; E21B 33/14; E21B 47/0005; E21B 47/14; G01N 33/383
(Continued)

(56) References Cited

U.S. PATENT DOCUMENTS 9,477,002 B2 * 10/2016 Miller .................... E21B 33/124
2009/0272530 A1 * 11/2009 Duguid ............... E21B 41/0064
166/250.17

(Continued)

FOREIGN PATENT DOCUMENTS

EP 2886794 A1 6/2015

OTHER PUBLICATIONS

Hayden R., "Case Studies in Evaluation of Cement with Wireline Logs in a Deep Water Environment", SPWLA 52nd Annual Logging Sympos, May 14-18, 2011, pp. 1-15.
(Continued)

*Primary Examiner* — Michael P Nghiem
(74) *Attorney, Agent, or Firm* — Sean K.M. Hinkley

(57) ABSTRACT

Systems, methods, and devices for evaluating proper cement installation in a well are provided. In one example, a method includes receiving acoustic cement evaluation data into a data processing system. The acoustic cement evaluation data derives from one or more acoustic downhole tools used over a depth interval in a well having a casing. The acoustic cement evaluation data includes sonic measurements and ultrasonic measurements. The method includes deriving a sonic-derived acoustic impedance Z(sonic) from the sonic measurements deriving an ultrasonic-derived acoustic impedance Z(ultrasonic) from the ultrasonic measurements comparing the Z(sonic) with respect to the Z(ultrasonic), and determining whether an annular fill behind the casing is well bonded, partially bonded, comprises wet microannulus, or comprises dry microannulus based on the comparison of the Z(sonic) with respect to the Z(ultrasonic).

20 Claims, 6 Drawing Sheets

(51) Int. Cl.
*G01V 5/04* (2006.01)
*G01V 9/00* (2006.01)
*G01V 1/50* (2006.01)
*E21B 33/14* (2006.01)
*E21B 47/00* (2012.01)
*E21B 47/14* (2006.01)
*G01N 33/38* (2006.01)
*G01V 1/52* (2006.01)

(52) U.S. Cl.
CPC ........... *E21B 47/14* (2013.01); *G01N 33/383* (2013.01); *G01V 1/52* (2013.01)

(58) Field of Classification Search
USPC .......................................................... 702/6
See application file for complete search history.

(56) References Cited

U.S. PATENT DOCUMENTS

| | | | | |
|---|---|---|---|---|
| 2013/0114377 | A1* | 5/2013 | Frisch | E21B 47/0005 367/35 |
| 2013/0155812 | A1* | 6/2013 | Froelich | E21B 47/0005 367/35 |
| 2013/0345983 | A1* | 12/2013 | Guo | G01V 5/104 702/8 |
| 2015/0177198 | A1* | 6/2015 | Thierry | G01V 1/44 166/253.1 |
| 2015/0218930 | A1* | 8/2015 | Zeroug | E21B 47/0005 367/26 |
| 2015/0219780 | A1* | 8/2015 | Zeroug | E21B 47/0005 702/6 |
| 2016/0061021 | A1* | 3/2016 | Shaposhnikov | E21B 47/0005 367/35 |
| 2016/0069181 | A1* | 3/2016 | van Kuijk | E21B 47/0005 702/11 |
| 2016/0109604 | A1* | 4/2016 | Zeroug | E21B 47/0005 367/13 |
| 2016/0245946 | A1* | 8/2016 | Kalyanraman | G01V 1/42 |
| 2016/0265340 | A1* | 9/2016 | Frisch | E21B 47/0005 |
| 2017/0108607 | A1* | 4/2017 | Frisch | E21B 47/0005 |
| 2017/0168183 | A1* | 6/2017 | Hayman | G01V 1/48 |
| 2017/0342817 | A1* | 11/2017 | Tello | E21B 47/0005 |
| 2018/0149019 | A1* | 5/2018 | Bose | G01V 1/50 |
| 2018/0156759 | A1* | 6/2018 | Lei | G01N 29/265 |
| 2018/0195980 | A1* | 7/2018 | Guo | G01N 23/05 |

OTHER PUBLICATIONS

Office Action issued in the related EP Application 15290288.8, dated Jan. 22, 2018 (5 pages).

Leslie et al., Coupling and Attenuation: A New Measurement Pair in Cement Bond Logging, SPE16207—SPE production operations symposium held in Oklahoma City, Oklahoma, Mar. 8-10, 1987 (8 pages).

Hayman et al., High-Resolution Cementation and Corrosion Imaging by Ultrasound, SPWLA 32nd Annual Logging Symposium, Jun. 16-19, 1991. (25 pages).

Pavel Shaposhinikov et al: "Advanced Techniques in Integrated Cement Evaluation", SPWLA 54th Annual Logging symposium, Jun. 22, 2013 (15 pages).

Jun Cai et al: "Solution to Cement Integrity Evaluation in Long-Extended Reach wells: New Record in South China", OTC-25027-MS, Mar. 25, 2014 (11 pages).

Extended European Search Report issued in the related EP Application EP15290288.8, dated May 2, 2016.

* cited by examiner

CEMENT EVALUATION USING THE INTEGRATION OF MULTIPLE MODES OF ACOUSTIC MEASUREMENTS

CROSS-REFERENCE TO RELATED APPLICATIONS

The present invention claims the benefits of European Patent Application No. 15290288.8, filed on Nov. 16, 2015, titled "Cement Evaluation Using the Integration of Multiple Modes of Acoustic Measurements," the entire content of which is hereby incorporated by reference into the current application.

BACKGROUND

This disclosure relates to evaluating cement behind a casing of a wellbore and, or particularly, to integrating multiple modes of acoustic measurements for cement evaluation.

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be read in this light.

A wellbore drilled into a geological formation may be targeted to produce oil and/or gas from certain zones of the geological formation. To prevent zones from interacting with one another via the wellbore and to prevent fluids from undesired zones entering the wellbore, the wellbore may be completed by placing a cylindrical casing into the wellbore and cementing the annulus between the casing and the wall of the wellbore. During cementing, cement may be injected into the annulus formed between the cylindrical casing and the geological formation. When the cement properly sets, fluids from one zone of the geological formation may not be able to pass through the wellbore to interact with one another. This desirable condition is referred to as "zonal isolation." Yet well completions may not go as planned. For example, the cement may not set as planned and/or the quality of the cement may be less than expected. In other cases, the cement may unexpectedly fail to set above a certain depth due to natural fissures in the formation.

A variety of acoustic tools may be used to determine well integrity, including verifying that cement is properly installed. These acoustic tools may use pulsed acoustic waves as they are lowered through the wellbore to obtain acoustic cement evaluation data (e.g., flexural attenuation, acoustic impedance measurements, etc.). Different modes of acoustic measurements may be measured in a range of acoustic frequencies. For example, some acoustic tools may be used to generate and measure sonic waveforms, ultrasonic waveforms, etc. Moreover, different modes of acoustic measurements may be particularly suitable for different conditions of the wellbore having different characteristics of mud, cement, and/or casing. While current techniques and modes of acoustic measurements may be suitable for various wellbore conditions, interpreting or discriminating more detailed cement characteristics may still be challenging.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

Embodiments of this disclosure relate to various systems, methods, and devices for evaluating an annular fill material in a well. Thus, the systems, methods, and devices of this disclosure describe various ways of using acoustic cement evaluation data obtained from acoustic downhole tools to evaluate annular integrity. In one example, a method includes receiving acoustic cement evaluation data into a data processing system. The acoustic cement evaluation data derives from one or more acoustic downhole tools used over a depth interval in a well having a casing. The acoustic cement evaluation data includes sonic measurements and ultrasonic measurements. The method includes deriving a sonic-derived acoustic impedance Z(sonic) from the sonic measurements deriving an ultrasonic-derived acoustic impedance Z(ultrasonic) from the ultrasonic measurements comparing the Z(sonic) with respect to the Z(ultrasonic), and determining whether an annular fill behind the casing is well bonded, partially bonded, comprises wet microannulus, or comprises dry microannulus based on the comparison of the Z(sonic) with respect to the Z(ultrasonic).

In another example, a computer-readable media includes instructions to receive sonic measurements and ultrasonic measurements from one or more acoustic downhole tools used in a depth interval of a well having a casing, determine a sonic acoustic impedance from the sonic measurements, determine an ultrasonic acoustic impedance from the ultrasonic measurement, compare the sonic acoustic impedance with the ultrasonic acoustic impedance, and based at least in part on the comparison of the sonic acoustic impedance and the ultrasonic acoustic impedance, classify an annulus behind the casing. The instructions further comprise instructions to: (a) classify the annulus as comprising well-bonded annular fill when the ultrasonic acoustic impedance is greater than an expected acoustic impedance and when the sonic acoustic impedance is approximately equal to the expected acoustic impedance; (b) classify the annulus as comprising wet microannulus when the ultrasonic acoustic impedance is less than or equal to the expected acoustic impedance and when the ultrasonic acoustic impedance is greater than the sonic acoustic impedance; (c) classify the annulus as comprising dry microannulus when the ultrasonic acoustic impedance is less than or equal to the expected acoustic impedance and when the ultrasonic acoustic impedance is significantly smaller than the sonic acoustic impedance; or (d) classify the annulus as comprising partially bonded annular fill when the ultrasonic acoustic impedance is less than or equal to the expected acoustic impedance and when the ultrasonic acoustic impedance is approximately equal to the sonic acoustic impedance.

Various refinements of the features noted above may be undertaken in relation to various aspects of the present disclosure. Further features may also be incorporated in these various aspects as well. These refinements and additional features may be determined individually or in any combination. For instance, various features discussed below in relation to the illustrated embodiments may be incorporated into any of the above-described aspects of the present disclosure alone or in any combination. The brief summary presented above is intended to familiarize the reader with certain aspects and contexts of embodiments of the present disclosure without limitation to the claimed subject matter.

BRIEF DESCRIPTION OF THE DRAWINGS

Various aspects of this disclosure may be better understood upon reading the following detailed description and upon reference to the drawings in which.

DETAILED DESCRIPTION

Figure 1:
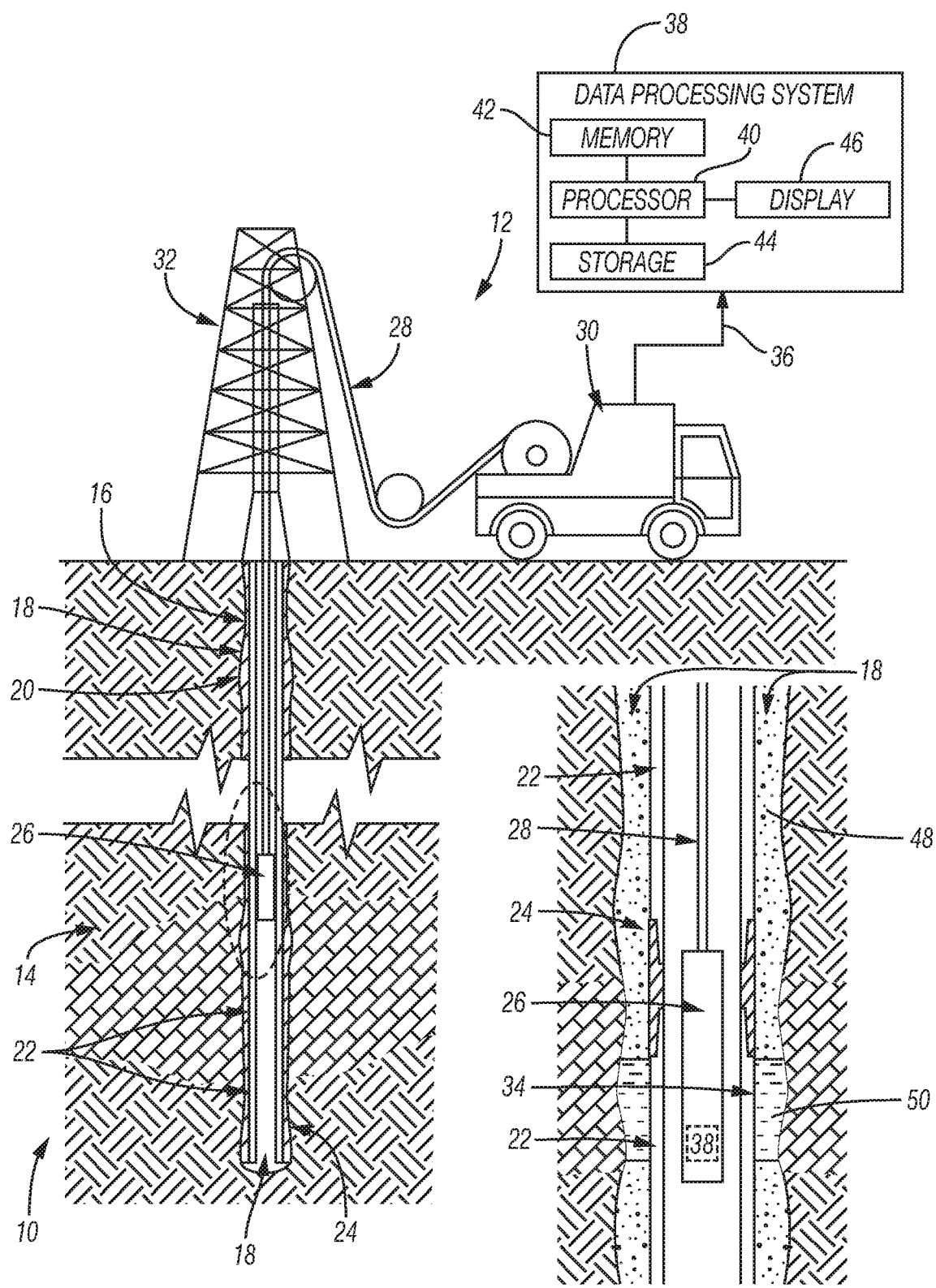
FIG. 1 is a schematic diagram of a system for verifying proper cement installation and/or zonal isolation of a well, in accordance with an embodiment.

One or more specific embodiments of the present disclosure will be described below. These described embodiments are examples of the presently disclosed techniques. Additionally, in an effort to provide a concise description of these embodiments, some features of an actual implementation may not be described in the specification. It should be appreciated that in the development of any such actual implementation, as in any engineering or design project, numerous implementation-specific decisions may be made to achieve the developers' specific goals, such as compliance with system-related and business-related constraints, which may vary from one implementation to another. Moreover, it should be appreciated that such a development effort might be complex and time consuming, but would still be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.

When a well is drilled, metal casing may be installed inside the well and cement placed into the annulus between the casing and the wellbore. When the cement sets, fluids from one zone of the geological formation may not be able to pass through the annulus of the wellbore to interact with another zone. This condition is referred to as "zonal isolation." Proper cement installation may also ensure that the well produces from targeted zones of interest. To verify that the cement has been properly installed, this disclosure teaches systems and methods for evaluating acoustic cement evaluation data. As used herein, "acoustic cement evaluation data" refers to any combination of acoustic attenuation data, acoustic amplitude data, acoustic impedance data, flexural attenuation data, and/or other types of acoustic data useful for well integrity analysis that may be obtained from one or more acoustic downhole tools, including tools using sonic measurements, ultrasonic measurements, or both.

The acoustic cement evaluation data that is obtained by the acoustic downhole tools may be parameterized based on initial assumptions on the characteristics of the well and/or the acoustic downhole tools and further processed to determine conditions of the well. For instance, the acoustic cement evaluation data may include an assumed characteristic of the annulus of the well. However, conventional processing techniques may not always use thorough and accurate assumptions on all well characteristics. For example, conventional techniques may not account for details such as characteristics of microannulus in the annulus in cement evaluation. Such microannuli may include gaps in the interface of the annular fill material and the casing, and may have different characteristics, such as being filled with liquid or gas to be characterized as wet or dry, for example. Yet parameterization errors or inaccuracies could incorrectly predict the actual conditions in the well. As a result, the acoustic cement evaluation data may not accurately reflect the true conditions of the well. In addition, log data may have other ambiguities or uncertainties which may also reduce accuracy in processing and predicting conditions of the well.

This disclosure teaches various ways to improve the investigation of annulus material in a well using an integration of multiple modes of acoustic measurements. One or more embodiments involve a workflow for integrating ultrasonic measurements and sonic measurements to evaluate characteristics of the annular material. In some embodiments, the acoustic impedance of the annular material may be derived from sonic attenuation measurements and/or from sonic amplitude measurements, and the sonic-derived acoustic impedance may be integrated with acoustic impedance derived from ultrasonic measurements and processed to determine further characteristics of the annulus acoustic impedance, such as whether the annulus acoustic impedance is attributable to fluids and/or solids and/or whether the annulus can be classified as having wet or dry microannulus, etc.

With this in mind, FIG. 1 schematically illustrates a system 10 for evaluating cement behind casing in a well. In particular, FIG. 1 illustrates surface equipment 12 above a geological formation 14. In the example of FIG. 1, a drilling operation has previously been carried out to drill a wellbore 16. In addition, an annular fill 18 (e.g., cement, resin, or any other material for filling the annulus 20) has been used to seal an annulus 20—the space between the wellbore 16 and casing joints 22 and collars 24—with cementing operations.

As seen in FIG. 1, several casing joints 22 (also referred to below as casing 22) are coupled together by the casing collars 24 to stabilize the wellbore 16. The casing joints 22 represent lengths of pipe, which may be formed from steel or similar materials. In one example, the casing joints 22 each may be approximately 13 m or 40 ft long, and may include an externally threaded (male thread form) connection at each end. A corresponding internally threaded (female thread form) connection in the casing collars 24 may connect two nearby casing joints 22. Coupled in this way, the casing joints 22 may be assembled to form a casing string to a suitable length and specification for the wellbore 16. The casing joints 22 and/or collars 24 may be made of carbon steel, stainless steel, or other suitable materials to withstand a variety of forces, such as collapse, burst, and tensile failure, as well as chemically aggressive fluid.

The surface equipment 12 may carry out various well logging operations to detect conditions of the wellbore 16. The well logging operations may measure parameters of the geological formation 14 (e.g., resistivity or porosity) and/or the wellbore 16 (e.g., temperature, pressure, fluid type, or fluid flowrate). Other measurements may provide acoustic cement evaluation data (e.g., flexural attenuation and/or acoustic impedance) that may be used to verify the cement installation and the zonal isolation of the wellbore 16. One or more acoustic logging tools 26 may obtain some of these measurements.

The example of FIG. 1 shows the acoustic logging tool 26 being conveyed through the wellbore 16 by a cable 28. Such a cable 28 may be a mechanical cable, an electrical cable, or an electro-optical cable that includes a fiber line protected against the harsh environment of the wellbore 16. In other examples, however, the acoustic logging tool 26 may be conveyed using any other suitable conveyance, such as coiled tubing. The acoustic logging tool 26 may be, for example, a Sonic Scanner, an UltraSonic Imager (USI) tool and/or an Isolation Scanner tool by Schlumberger Technology Corporation. The acoustic logging tool 26 may obtain measurements of acoustic impedance from ultrasonic waves and/or flexural attenuation. For instance, the acoustic logging tool 26 may obtain a pulse echo measurement that exploits the thickness mode (e.g., in the manner of an ultrasonic imaging tool) or may perform a pitch-catch measurement that exploits the flexural mode (e.g., in the manner of an imaging-behind-casing (IBC) tool). These measurements may be used as acoustic cement evaluation data in a solid-liquid-gas (SLG) model map to identify likely locations where solid, liquid, or gas is located in the annulus 20 behind the casing 22.

The acoustic logging tool 26 may be deployed inside the wellbore 16 by the surface equipment 12, which may include a vehicle 30 and a deploying system such as a drilling rig 32. Data related to the geological formation 14 or the wellbore 16 gathered by the acoustic logging tool 26 may be transmitted to the surface, and/or stored in the acoustic logging tool 26 for later processing and analysis. As will be discussed further below, the vehicle 30 may be fitted with or may communicate with a computer and software to perform data collection and analysis.

FIG. 1 also schematically illustrates a magnified view of a portion of the cased wellbore 16. As mentioned above, the acoustic logging tool 26 may obtain acoustic cement evaluation data relating to the presence of solids, liquids, or gases behind the casing 22. For instance, the acoustic logging tool 26 may obtain measures of acoustic impedance and/or flexural attenuation, which may be used to determine where the material behind the casing 22 is a solid (e.g., properly set cement) or is not solid (e.g., is a liquid or a gas). When the acoustic logging tool 26 provides such measurements to the surface equipment 12 (e.g., through the cable 28), the surface equipment 12 may pass the measurements as acoustic cement evaluation data 36 to a data processing system 38 that includes a processor 40, memory 42, storage 44, and/or a display 46. In other examples, the acoustic cement evaluation data 36 may be processed by a similar data processing system 38 at any other suitable location. For example, in some embodiments, all or a portion of the data processing system 38 may be coupled to the acoustic tool 26, and some or all of the cement evaluation data processing may occur in the wellbore 16.

The data processing system 38 may collect the acoustic cement evaluation data 36 and determine well integrity based on processing of the data 36. For example, the acoustic cement evaluation data 36 may be processed to derive certain characteristics of the annular fill 18, such as to determine an acoustic impedance of the annular fill. Additionally, the data processing system 38 may integrate multiple types of acoustic cement evaluation data 36, including multiple modes of acoustic data 36 obtained with different types of acoustic tools 26, such as those suitable for measuring sonic and/or ultrasonic measurements. To do this, the processor 40 may execute instructions stored in the memory 42 and/or storage 44. As such, the memory 42 and/or the storage 44 of the data processing system 38 may be any suitable article of manufacture that can store the instructions. The memory 42 and/or the storage 44 may be ROM memory, random-access memory (RAM), flash memory, an optical storage medium, or a hard disk drive, to name a few examples. The display 46 may be any suitable electronic display that can display the logs and/or other information relating to classifying the material in the annulus 20 behind the casing 22.

In this way, the acoustic cement evaluation data 36 from the acoustic logging tool 26 may be used to determine whether the annular fill 18 has been installed as expected. In some cases, the acoustic cement evaluation data 36 may indicate that the cement of the annular fill 18 has a generally solid character (e.g., as indicated at numeral 48) and therefore has properly set. In other cases, the acoustic cement evaluation data 36 may indicate the potential absence of cement or that the annular fill 18 has a generally liquid or gas character (e.g., as indicated at numeral 50), which may imply that the cement of the annular fill 18 has not properly set. For example, when the indicate the annular fill 18 has the generally liquid character as indicated at numeral 50, this may imply that the cement is either absent or was of the wrong type or consistency, and/or that fluid channels have formed in the cement of the annular fill 18.

In some embodiments, processing acoustic cement evaluation data 36 by integrating various types of acoustic data, such as sonic measurements (e.g., sonic attenuation, sonic amplitude, etc.) with ultrasonic measurements (e.g., ultrasonic acoustic impedance, ultrasonic attenuation, etc.) may result in more accurate and/or more precise cement evaluation than processing one set of data alone. The present techniques involve using acoustic cement evaluation data 36 to indicate additional details when the annular fill 18 is partially bonded and/or when microannuli are present in the annular fill 18. For example, in some embodiments, the data 36 may be processed to further characterize microannuli, such as discriminate between regions having wet microannulus and dry microannulus.

Figure 2:
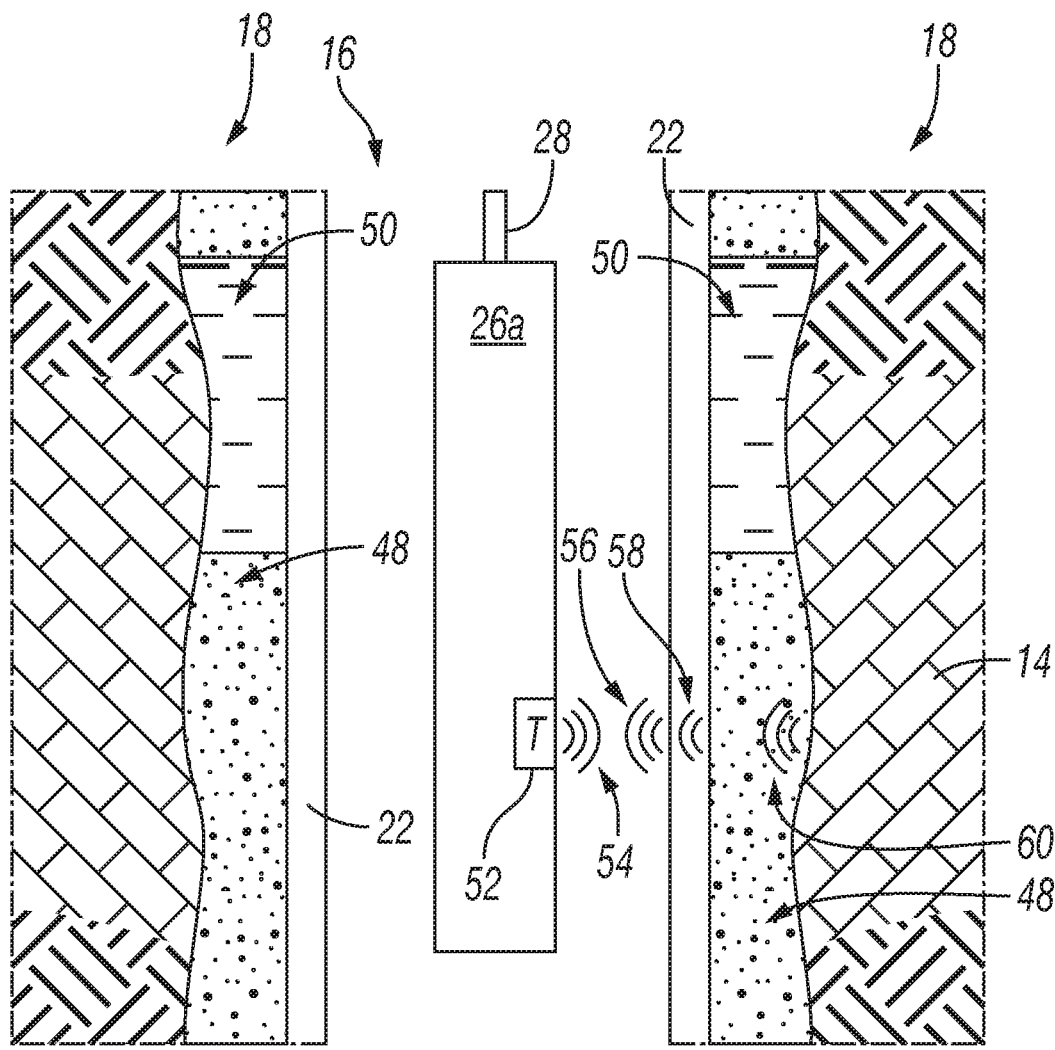
FIG. 2 is a block diagram of an acoustic downhole tool to obtain acoustic cement evaluation data relating to material behind casing of the well, in accordance with an embodiment.

With this in mind, FIG. 2 provides a general example of the operation of the acoustic logging tool 26a in the wellbore 16. Specifically, a transducer 52 in the acoustic logging tool 26 may emit acoustic waves 54 out toward the casing 22. Reflected waves 56, 58, and 60 may correspond to interfaces at the casing 22, the annular fill 18, and the geological formation 14 or an outer casing, respectively. The reflected waves 56, 58, and 60 may vary depending on whether the annular fill 18 is of the generally solid character 48 or the generally liquid or gas character 50. The acoustic logging tool 26 may use any suitable number of different techniques, including measurements of acoustic impedance from sonic waves, ultrasonic waves and/or flexural attenuation. When one or more of these measurements of acoustic cement evaluation data are obtained, they may be integrated and/or processed to determine characteristics of the annular fill 18.

Figure 3:
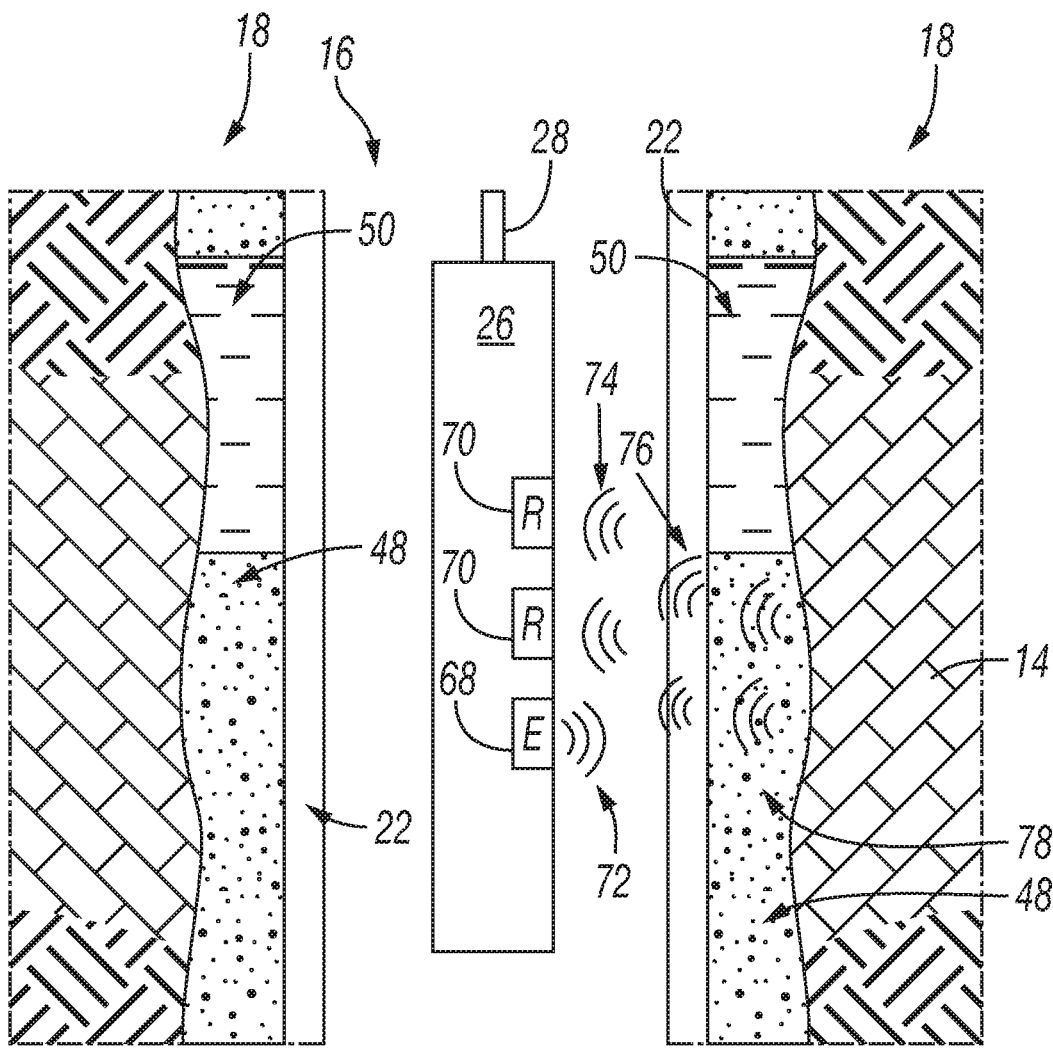
FIG. 3 is a block diagram of another acoustic downhole tool to obtain acoustic cement evaluation data relating to material behind casing of the well, in accordance with an embodiment.

FIG. 3 provides another example embodiment of the acoustic logging tool 26b having an emitter 68 and a pair of receiver transducers 70. The emitter 68 in the acoustic logging tool 26a may emit acoustic energy 72 out toward the casing 22 resulting in reflected waves 74, 76, and 78. In the embodiments shown in FIG. 2, the emitted energy excites a predominantly zeroth-order asymmetric mode (also referred to as flexural mode). As in the embodiment described above, the acoustic waves 72 propagate via transmission into both sides of the casing wall 22. The transmission in the casing annulus depends on the material on the outer side of the casing wall with a different amount of energy leak inside the annulus. The acoustic logging tool embodiment depicted in FIG. 3 may use measurements of acoustic impedance from flexural attenuation. The different distance from the emitter 68 and the two receiver transducers 70 and the energy leak induce different amplitudes on the measured acoustic pressure.

In accordance with the present techniques, acoustic cement evaluation data 36 may be obtained from the acoustic logging tool 26a, 26b, and/or any other suitable acoustic logging tool, referred to generally as tool 26, which may measure sonic, ultrasonic, or a combination of acoustic measurements. Different acoustic measurements may be processed and integrated to determine further characteristics of the annular fill 18. One or more embodiments involve the integration of sonic measurements with ultrasonic measurements to classify sections of the annulus as having a well cemented section, wet microannulus, dry microannulus, and/or channels with partial bonds.

Figure 4:
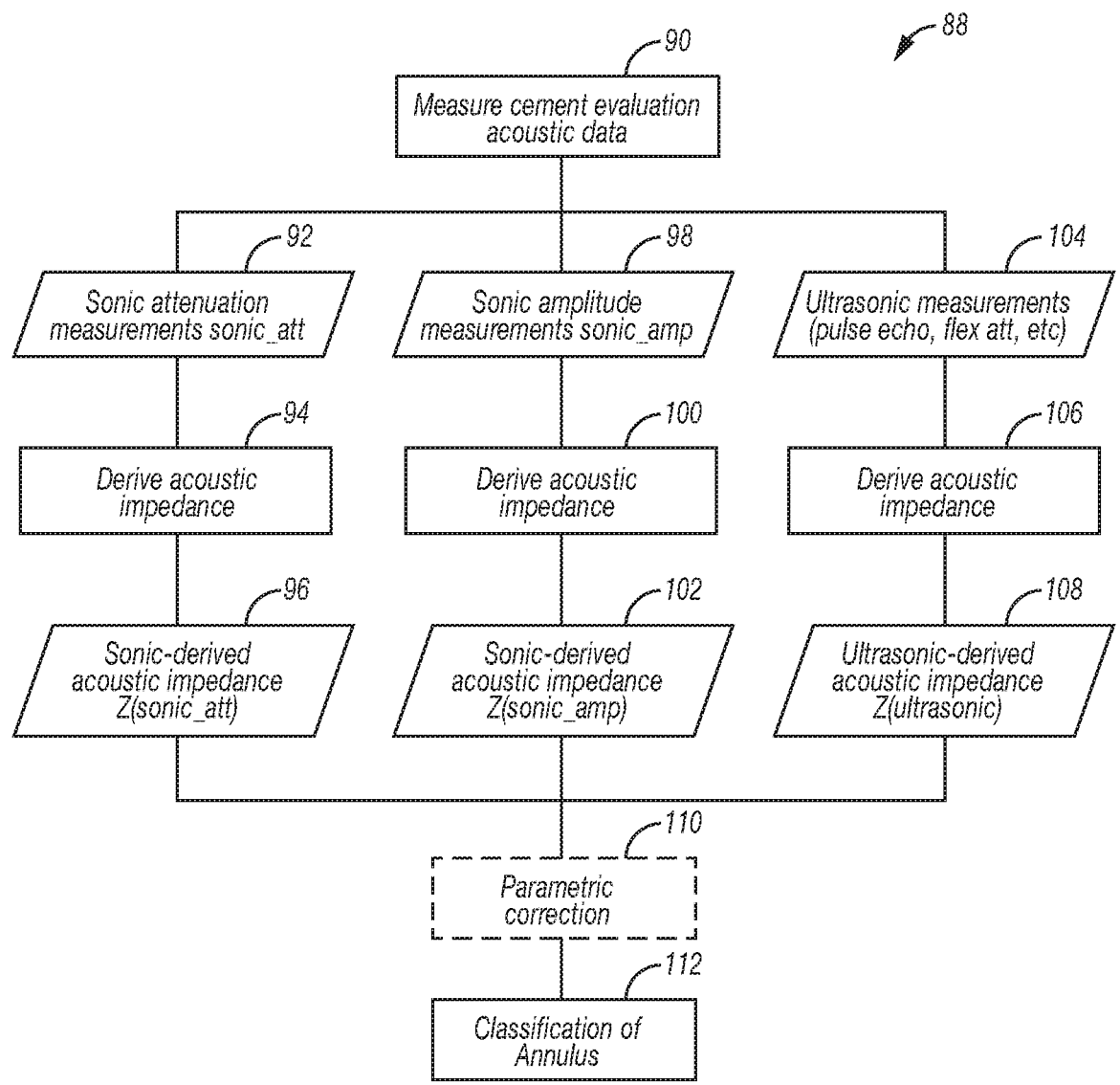
FIG. 4 is a workflow for classifying an annulus in a wellbore based on an integration of sonic-derived and ultrasonic-derived acoustic impedances, in accordance with an embodiment.

Acoustic cement evaluation data may be processed in various ways to result in further details and classifications of the annular fill 18. For instance, as shown by a workflow 88 of FIG. 4, the acoustic cement evaluation data may be obtained by measurements using one or more acoustic tools 26 (block 90). These measured acoustic cement evaluation data may include, for example, sonic attenuation measurements 92, sonic amplitude measurements 98, and ultrasonic measurements 104, or some combination of these measurements. For example, in some embodiments, only one type of sonic measurement 92 or 98 may be used in the workflow 88 to determine details and classifications of the annular fill 18.

The sonic attenuation measurements 92, referred to as sonic_att, may be processed to derive (block 94) acoustic impedance of the annular fill 18, referred to as sonic_att-derived acoustic impedance, or Z(sonic_att) 96. The derivation (block 94) of acoustic impedance 96 from sonic attenuation measurements 92 may be based on the casing extensional mode having nearly zero sensitivity to compressional coupling. As the compressional coupling effect on casing extensional mode is negligible, the sonic attenuation measurements may represent a free-pipe reading (i.e., a portion of the casing 22 that is not surrounded by annular fill 18) as soon as the annular fill 18 loses its shear coupling to the casing 22. Once the shear coupling is lost, either due to de-bonding of the annular fill from the casing or due to changes in material (e.g., from solid to fluid or gas behind the casing at the casing and cement interface, the sonic attenuation measurements may no longer be effective for computing the acoustic impedance of the annular fill. Extending the attenuation formula to relatively low values of acoustic impedance may still allow for the calculation of acoustic impedance if the annular fill 18 maintains the finite shear velocity and shear coupling of the sonic waves. Sonic attenuation measurements may be insensitive to gas or fluid, because the casing extensional mode is insensitive to compressional properties. Therefore, in some embodiments, the processing of sonic attenuation measurements 92 may involve processing sonic_att 92 to first determine sonic amplitude 98, as attenuation-based measurements alone may not discriminate between liquids and gases. Furthermore, in some embodiments, sonic attenuation 92 may be computed from sonic amplitude 98 at multiple receivers. Therefore, the sonic attenuation 92 may implicitly include information related to sonic amplitude 98, and such sonic attenuation 92 measurements may also be processed to discriminate between liquids and gases.

The sonic amplitude measurements 98, referred to as sonic_amp, may also be processed to derive (block 100) acoustic impedance of the annular fill 18, referred to as sonic_amp-derived acoustic impedance, or Z(sonic_amp) 102. The derivation (block 100) of acoustic impedance 102 from sonic amplitude measurements 98 may be based on the sonic amplitude measurements 98 having sensitivity to both casing mode attenuation and coupling attenuation. Coupling attenuation may be largely sensitive to acoustic impedance and compressional coupling of solids. Different sonic amplitude measurements 98 (also known as cement bond logs, or "CBL measurements") may be expected when the casing annulus is air or water due to the different and known acoustic impedances of air and water. The coupling attenuation may be sensitive not only to acoustic coupling but also to the geometries within the annulus (e.g., microannulus gap size). For example, sonic amplitude measurements 98 may change gradually (e.g., from approximately 38 mV to 62 mV in free-pipe) when the annular gap is increased from approximately 0 to 10 mm. An acoustic impedance derived from sonic_amp 98 may also be affected by fluid properties due to the sensitivity of the sonic_amp 98 to fluid, and some embodiments involve compensating for this characteristic. The sonic_amp 98 may be increased by approximately 30-40% when gas or air is present behind casing, at least in part due to significantly low coupling attenuation.

The acoustic impedances Z(sonic_att) 96 and Z(sonic_amp) 102 derived from sonic_att 92 and sonic_amp 98, respectively, may in some circumstances be interpreted or applied differently in characterizing the annular fill 18. Both acoustic impedances 96, 102 may be representative of the planned acoustic impedance of the annular material 18 in a region where the annular fill 18 is well bonded (e.g., in the absence of free pipe or microannuluses in the annular fill 18). In some circumstances, the Z(sonic_att) 96 may represent free-pipe values not only when there is actually free-pipe, but also when the annular fill includes microannulus (dry or wet), highly contaminated and poorly set (or unset) cement with only compressional coupling and no shear coupling. Z(sonic_att) values 96 may also be varying or inconclusive in the presence of azimuthal heterogeneity, partial cement bonding, or presence of channels in the annular fill 18.

Z(sonic_amp) values 102 may represent liquids (e.g., mud or gas) when the annulus is filled with liquid. However, the Z(sonic_amp) 102 may vary between acoustic impedances of liquid and cement in the presence of microannuli, depending on the size of the microannuli and the material filling them (e.g., wet or dry microannuli). The Z(sonic_amp) 102 may also return varying or inconclusive in the presence of azimuthal heterogeneity, partial cement bonding, or presence of channels in the annular fill 18. Z(sonic_amp) values 102 may also represent air if the annular gap is larger than debonding or in the presence of very small microannuli.

While Z(sonic_att) 96 and Z(sonic_amp) 102 may be derived from different computations and/or from different measurements and may be interpreted differently, Z(sonic_att) 96 and Z(sonic_amp) 102 may also be referred to as simply Z(sonic), representing the acoustic impedance of annular fill 18 that is derived from a sonic measurement, including sonic amplitude measurements 98 or sonic attenuation measurements 92 or both.

The ultrasonic measurements 104 may include, for example, pulse-echo measurements, flexural attenuation, or any other suitable ultrasonic measurement. The workflow 88 may involve deriving (block 106) acoustic impedance 108 from ultrasonic measurements 104, resulting in ultrasonic-derived acoustic impedance, referred to as Z(ultrasonic) 108. In some embodiments, Z(ultrasonic) 108 may be further processed. For example, ultrasonic measurements 104 and/or Z(ultrasonic) 108 may be filtered, averaged, and/or different modalities of ultrasonic measurements 104 (e.g., pulse echo, flexural attenuation, etc.) may be combined or processed to obtain a Z(ultrasonic) 108 to be used in the workflow 88.

In accordance with the present techniques, the workflow 88 may involve integrating Z(sonic) 96, 102 with Z(ultrasonic) 108 to determine more information about the annular fill 18. In some embodiments, the Z(sonic) 96, 102 and Z(ultrasonic) 108 may be parametrically corrected (block 110) for processing, though in some embodiments, this correction may not be performed. For example, in some embodiments, the Z(sonic) 96, 102 and Z(ultrasonic) 108 may already be sufficiently accurate for the workflow 88.

The correction (block 110), when performed, may involve providing correction and/or quality control of the impedance values by manual and/or automatic correction of the Z(sonic) 96, 102 and Z(ultrasonic) 108 to result in optimum parameters based on the distribution of Z(sonic) 96, 102 and Z(ultrasonic) 108 that will lead to reliable estimation of annulus acoustic impedance attributable to fluids and solids in the annulus.

In some embodiments, the parametric correction (block 110) may involve free-pipe analysis. The acoustic impedances 96, 102, and 108 derived from acoustic measurements measured at a free-pipe region should be comparable to the acoustic impedances of the liquids or gases, depending on the fluid in the annulus. Processing parameters for the both sonic and ultrasonic acoustic impedances 96, 102, and 108 may be corrected using a weighted scheme or a user-selected scheme depending on the reliability of a particular measurement in a particular situation. For example, if a free-pipe measurement of a sonic acoustic impedance and ultrasonic impedance is obtained and a sonic measurement from which the sonic acoustic impedance is derived is known to have very low uncertainty, then the acoustic impedance estimated from the ultrasonic measurements Z(ultrasonic) 108 may be corrected with respect to the relatively low-uncertainty Z(sonic) 96, 102. Similarly, if a free-pipe measurement is obtained and the ultrasonic measurement from which the ultrasonic acoustic impedance is derived is known to have very low uncertainty, then the acoustic impedance estimated from the sonic measurements Z(sonic) 96, 102 may be corrected with respect to the relatively low-uncertainty Z(ultrasonic) 108.

Whether or not the acoustic cement evaluation data is parametrically corrected, the data may be used for classification (block 112) of the annulus. As discussed, the acoustic impedances 96, 102 derived from sonic attenuation 92 or sonic amplitude 98 may represent different sensitivities to the annulus characteristics (e.g., different sensitivity to microannuli). As such, in some embodiments, different analyses may be used in the integration of sonic and ultrasonic measurements, depending on the type of sonic measurements used. The charts in FIGS. 5 and 6 represent the different behavior of acoustic impedance depending on characteristic of the sonic measurement 92 or 98.

Figure 5:
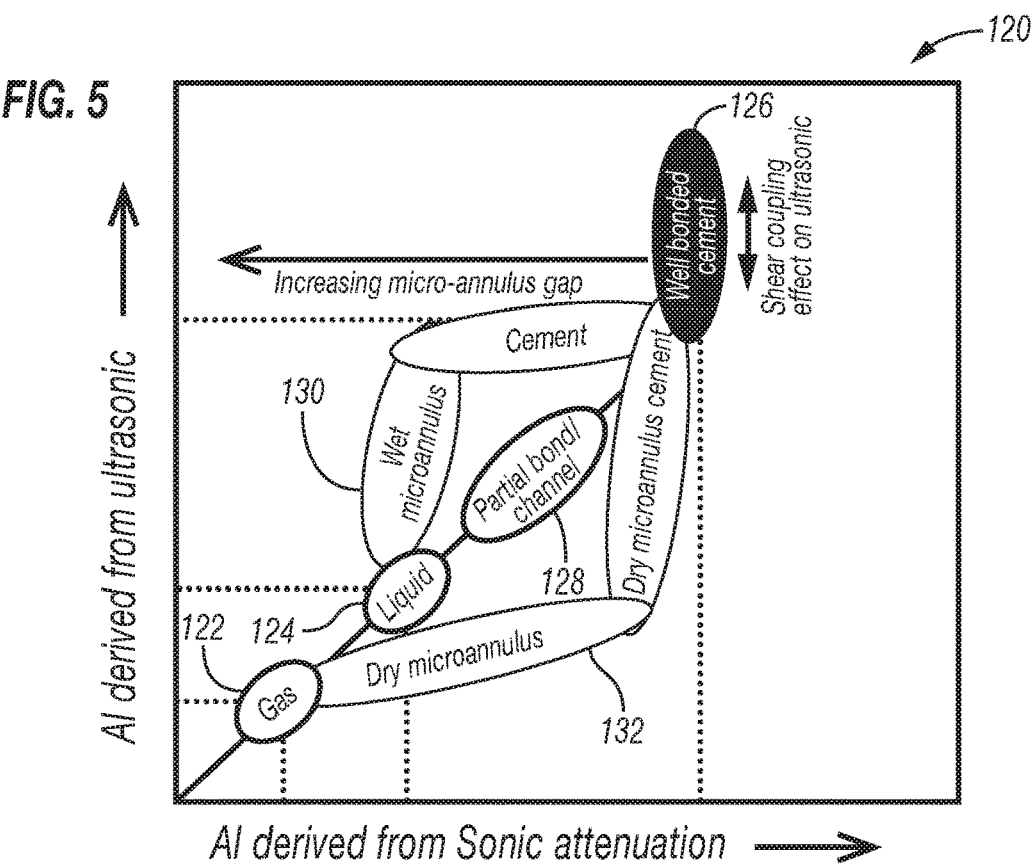
FIG. 5 is a plot illustrating a relationship between acoustic impedances determined from ultrasonic measurements and sonic attenuation measurements for evaluating an annulus, in accordance with an embodiment.

The chart 120 in FIG. 5 represents an integration of acoustic impedance derived from ultrasonic measurements Z(ultrasonic) 108 plotted with respect to acoustic impedance derived from sonic attenuation measurements Z(sonic_att) 96. The zones 122, 124, 126, 128, 130, 132 represent different classifications of the annulus based on the intersection and/or integration of Z(ultrasonic) 108 and Z(sonic_att) 96 at a region where the corresponding ultrasonic and sonic measurements were measured in the wellbore 16. For example, depending on the integration of Z(ultrasonic) 108 and Z(sonic_att) 96 and using the chart 120, a region may be characterized as having a gas zone 122, a liquid zone 124, or a zone of well-bonded cement 126. Additionally, due to the integration of Z(ultrasonic) 108 and Z(sonic_att) 96, additional features of the cemented region may be determined. In some embodiments, based on the integration of Z(ultrasonic) 108 and Z(sonic_att) 96, the workflow 88 may determine whether a region includes a zone of partial bonding or channels 128, a zone annular fill having wet microannulus 130, and/or a zone of annular fill having dry microannulus 132.

Figure 6:
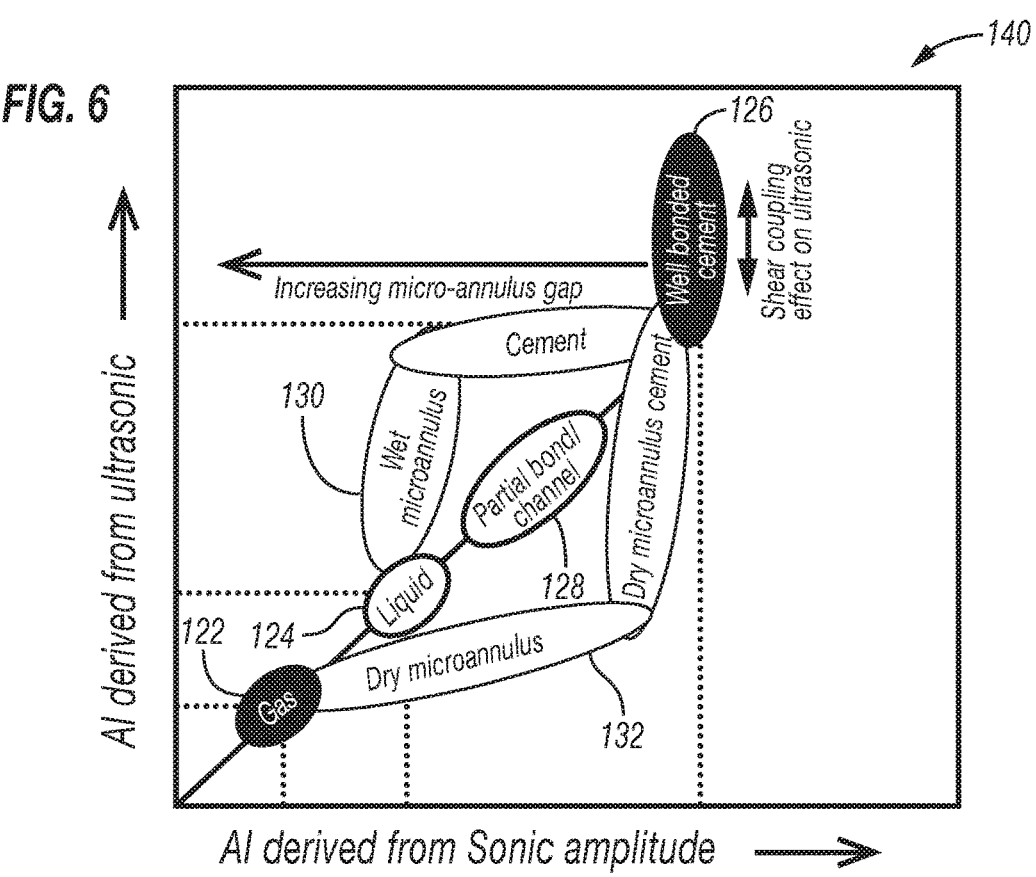
FIG. 6 is a plot illustrating a relationship between acoustic impedances determined from ultrasonic measurements and sonic amplitude measurements for evaluating an annulus, in accordance with an embodiment.

The chart 140 of FIG. 6 represents an integration of acoustic impedance derived from ultrasonic measurements Z(ultrasonic) 108 plotted with respect to acoustic impedance derived from sonic amplitude measurements Z(sonic_amp) 102. As with the chart 120 of FIG. 5, the chart 140 of FIG. 6 also includes zones 122, 124, 126, 128, 130, 132 representing different classifications of the annulus based on the intersection and/or integration of Z(ultrasonic) 108 and Z(sonic_amp) 102 at a region where the corresponding ultrasonic and sonic measurements were measured in the wellbore 16. For example, depending on the integration of Z(ultrasonic) 108 and Z(sonic_amp) 102 and using the chart 140, a region may be characterized as having a gas zone 122, a liquid zone 124, or a zone of well-bonded cement 126. Additionally, due to the integration of Z(ultrasonic) 108 and Z(sonic_amp) 102, additional features of the cemented region may be determined. In some embodiments, based on the integration of Z(ultrasonic) 108 and Z(sonic_amp) 102, the workflow 88 may determine whether a region includes a zone of partial bonding or channels 128, a zone annular fill having wet microannulus 130, and/or a zone of annular fill having dry microannulus 132.

Figure 7:
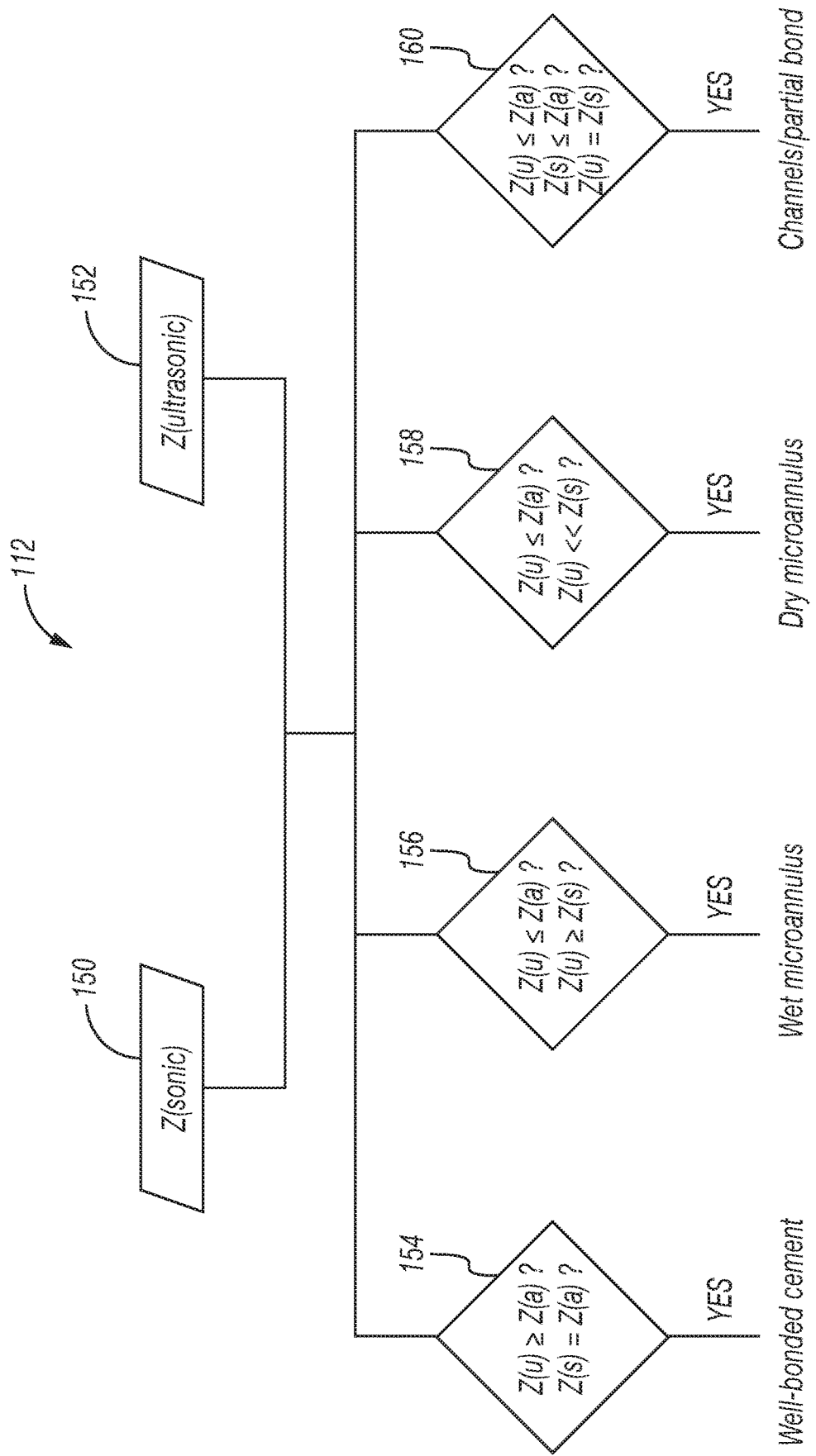
FIG. 7 is flowchart for classifying an annulus, in accordance with an embodiment.

The flowchart 112 in FIG. 7 provides a different representation for the classification of annulus as represented in the charts 120 and 140. The flowchart 112 may be a continuation of the classification (block 112) step in the workflow 88 of FIG. 4. Parametrically corrected acoustic impedances Z(sonic) 150 and Z(ultrasonic) 152 may be used for the classification, though this may not always be used in some embodiments. Whether or not the acoustic impedances are parametrically corrected, Z(sonic) 150 and Z(ultrasonic) 152 may be evaluated and compared, as represented by decision blocks 154, 156, 158, and 160. In some embodiments, Z(sonic) 150 and/or Z(ultrasonic) 152 may be compared with a known acoustic impedance of the annular fill, referred to as Z(a). Z(a) may be an expected, estimated, or planned acoustic impedance of the annular fill, based on known characteristics of the annular fill.

In some embodiments, the flowchart 112 for classifying the annulus involves determining whether the ultrasonic-derived acoustic impedance Z(ultrasonic) 152 is greater than or equal to Z(a) and determining whether the sonic-derived acoustic impedance Z(sonic) 150 is approximately the same as Z(a). Z(ultrasonic) may be expected to be greater than Z(a) due to the expected shear coupling in the annular fill 18. Therefore, if the conditions Z(ultrasonic) 152≥Z(a) and Z(sonic) 150=Z(a) are met, as represented by decision block 154, then the region may be classified as having well-bonded cement.

If Z(ultrasonic) 152 is less than or equal to Z(a), then the shear coupling expected in the annular fill 18 may not be present, which may be due to different situations or characteristics in the annular fill 18. If the Z(ultrasonic) 152 is less than or equal to Z(a), then the flowchart 112 may further compare Z(ultrasonic) 152 with respect to Z(sonic) 150. The workflow 112 may determine (block 156) whether Z(ultrasonic) 152 is greater than Z(sonic) 150, which may be indicative of the annular fill 18 having wet microannulus. Conversely, if Z(ultrasonic) 152 is significantly smaller than Z(sonic) 150, the workflow 112 may determine (block 158) this to be indicative of the annular fill 18 having dry microannulus. One explanation of this is that ultrasonic measurements are more sensitive to gas and responds earlier to dry microannuli.

Finally, if Z(ultrasonic) 152 is less than or equal to Z(a), and if Z(ultrasonic) 152 is approximately the same as Z(sonic) 150, then the workflow 112 may determine (block 160) this indicative of the annular fill 18 is partially bonded and/or has channels. The workflow 112 may further make or verify this determination if Z(sonic) 150 is less than or equal to Z(a).

Further refinements are possible, including using further processing or analyses to make even more appropriate classifications of the annulus based on the integration of ultrasonic and sonic measurements. For instance, further corrections may be made to either or both sets of data, and in some embodiments, more than two types of measurements may be integrated to make annular classifications.

The specific embodiments described above have been shown by way of example, and it should be understood that these embodiments may be susceptible to various modifications and alternative forms. It should be further understood that the claims are not intended to be limited to the particular forms disclosed, but rather to cover modifications, equivalents, and alternatives falling within the spirit and scope of this disclosure.

The invention claimed is:

1. A method comprising:
measuring acoustic cement evaluation data with one or more acoustic downhole tools used over a depth interval in a well having a casing, wherein the acoustic cement evaluation data comprises sonic measurements and ultrasonic measurements,
receiving the acoustic cement evaluation data into a data processing system;
deriving a sonic-derived acoustic impedance Z(sonic) from the sonic measurements;
deriving an ultrasonic-derived acoustic impedance Z(ultrasonic) from the ultrasonic measurements;
comparing the Z(sonic) with respect to the Z(ultrasonic) to determine if Z(sonic) is greater, less than or equal to Z(ultrasonic); and
determining whether an annular fill behind the casing is well bonded, partially bonded, comprises wet microannulus, or comprises dry microannulus based on the comparison of the Z(sonic) with respect to the Z(ultrasonic).

2. The method of claim 1, wherein the ultrasonic measurements comprises flexural attenuation.

3. The method of claim 1, wherein the ultrasonic measurements comprises pulse echo measurements.

4. The method of claim 1, wherein the sonic measurements comprise sonic attenuation measurements.

5. The method of claim 1, wherein the sonic measurements comprise sonic amplitude measurements.

6. The method of claim 1, comprising performing a parametric correction on the Z(sonic), the Z(ultrasonic), or both.

7. The method of claim 6, wherein performing the parametric correction comprises using a free-pipe measurement of the Z(sonic) and the Z(ultrasonic) and correcting one of the Z(sonic) or the Z(ultrasonic) based on the free-pipe measurement of the other.

8. The method of claim 1, including determining the annular fill is well-bonded when the Z(ultrasonic) is greater than or equal to an expected acoustic impedance of the annular fill and when the Z(sonic) is substantially similar to the expected acoustic impedance.

9. The method of claim 1, including determining the annular fill comprises wet microannulus when the Z(ultrasonic) is less than or equal to an expected acoustic impedance of the annular fill and when the Z(ultrasonic) is greater than Z(sonic).

10. The method of claim 1, including-determining the annular fill comprises dry microannulus when the Z(ultrasonic) is less than or equal to an expected acoustic impedance of the annular fill and when the Z(ultrasonic) is significantly less than Z(sonic).

11. The method of claim 1, including determining the annular fill is partially bonded when the Z(ultrasonic) is less than or equal to an expected acoustic impedance of the annular fill and when the Z(ultrasonic) is approximately the same as Z(sonic).

12. The method of claim 1, including determining the annular fill is partially bonded when the Z(ultrasonic) is less than or equal to an expected acoustic impedance of the annular fill and when the Z(sonic) is less than or equal to the expected acoustic impedance.

13. A system comprising:
one or more acoustic downhole tools used over a depth interval in a well having a casing to obtain acoustic cement evaluation data relative to the well, wherein the acoustic cement evaluation data comprises sonic measurements and ultrasonic measurements
a data processing system configured to:
receive sonic measurements and ultrasonic measurements from one or more acoustic downhole tools used in a depth interval of a well having a casing;
determine a sonic acoustic impedance Z(sonic) from the sonic measurements;
determine an ultrasonic acoustic impedance Z(ultrasonic) from the ultrasonic measurements;
compare the sonic acoustic impedance with the ultrasonic acoustic impedance to determine if Z(sonic) is greater, less than or equal to Z(ultrasonic); and based at least in part on the comparison of the sonic acoustic impedance and the ultrasonic acoustic impedance, classify an annulus behind the casing.

14. The system of claim 13, wherein the data processing system is configured to classify the annulus as comprising well-bonded annular fill when the ultrasonic acoustic impedance is greater than an expected acoustic impedance and when the sonic acoustic impedance is approximately equal to the expected acoustic impedance.

15. The system of claim 13, wherein the data processing system is configured to classify the annulus as comprising wet microannulus when the ultrasonic acoustic impedance is less than or equal to the expected acoustic impedance and when the ultrasonic acoustic impedance is greater than the sonic acoustic impedance.

16. The system of claim 13, wherein the data processing system is configured to classify the annulus as comprising dry microannulus when the ultrasonic acoustic impedance is less than or equal to the expected acoustic impedance and when the ultrasonic acoustic impedance is significantly smaller than the sonic acoustic impedance.

17. The system of claim 13, wherein the data processing system is configured to classify the annulus as comprising partially bonded annular fill when the ultrasonic acoustic impedance is less than or equal to the expected acoustic impedance and when the ultrasonic acoustic impedance is approximately equal to the sonic acoustic impedance.

18. The system of claim 13, wherein the data processing system is configured to classify the annulus as comprising partially bonded annular fill when the ultrasonic acoustic impedance is less than or equal to the expected acoustic impedance and when the ultrasonic acoustic impedance is approximately equal to the sonic acoustic impedance and when the sonic acoustic impedance is smaller than or equal to the expected acoustic impedance.

19. The system of claim 13, wherein the data processing system is configured to parametrically correct the ultrasonic acoustic impedance, the sonic acoustic impedance, or both.

20. The system of claim 13, wherein the data processing system is configured to perform parametric correction on the Z(sonic), the Z(ultrasonic), or both based on a free-pipe measurement of the Z(sonic) and the Z(ultrasonic), wherein the parametric correction of one of the Z(sonic) or the Z(ultrasonic) is based on the free-pipe measurement of the other.

* * * * *